(12) United States Patent
Hand et al.

(10) Patent No.: US 6,488,630 B1
(45) Date of Patent: Dec. 3, 2002

(54) ARRAYS OF QUASI-RANDOMLY DISTRIBUTED ULTRASOUND TRANSDUCERS

(75) Inventors: Jeffrey Warren Hand, London (GB); Leonid Rafailovich Gavrilov, Moscow (RU)

(73) Assignee: Imperial College Innovations Limited (GB)

( * ) Notice: Subject to any disclaimer, the term of this patent is extended or adjusted under 35 U.S.C. 154(b) by 0 days.

(21) Appl. No.: 09/913,965

(22) PCT Filed: Feb. 17, 2000

(86) PCT No.: PCT/GB00/00563

§ 371 (c)(1),
(2), (4) Date: Jan. 4, 2002

(87) PCT Pub. No.: WO00/49598

PCT Pub. Date: Aug. 24, 2000

(30) Foreign Application Priority Data

Feb. 19, 1999 (GB) .............................................. 9903710

(51) Int. Cl.⁷ .................................................. A61B 8/00
(52) U.S. Cl. ...................................................... 600/459
(58) Field of Search ........................ 600/459; 29/25.35; 367/140, 153, 138

(56) References Cited

PUBLICATIONS

Goss et al. "Sparse Rnagdom Ultrasound Phased Array for Focal Surgery", Nov. 1996, vol. 43, No. 6, pp. 1111–1119.*
Journal of the Acoustical Society of America, vol. 95, Jan. 1994, (USA) D. McGehee, et al., "Beamforming with dense random arrays" pp. 318–323 especially p. 320 section "A. Method".

\* cited by examiner

*Primary Examiner*—Marvin M. Lateef
*Assistant Examiner*—Ruby Jain
(74) *Attorney, Agent, or Firm*—Nikolai & Mersereau, P.A.

(57) ABSTRACT

An ultrasound transducer array suitable for medical uses such as tissue ablation and short duration high intensity hyperthermia has a plurality of ultrasound transducer elements dispersed across a substrate surface for focusing ultrasound energy over a predetermined focal volume. Particularly optimal results are obtained where the elements are dispersed over the substrate surface in a quasi-random distribution, where the total radiating area of the elements occupying between approximately 40 and 70 % of the total array area, and the frequency of operation of the ultrasound elements and the average diameter of the elements are related according to the expression: $d = A \times c / f$.

21 Claims, 7 Drawing Sheets

ARRAYS OF QUASI-RANDOMLY DISTRIBUTED ULTRASOUND TRANSDUCERS

The present invention relates to transducer arrays for generating and focusing ultrasound energy distributions.

There has recently been much interest in developing minimally invasive therapeutic ultrasound techniques for surgery (eg. tissue ablation) or short duration high-intensity hyperthermia, since these may offer potential benefits compared with conventional approaches in terms of reduced morbidity, increased patient acceptability and reduced in-patient time.

Much of the work reported in the field of ultrasound induced ablation has involved the use of single, or a few, piezoceramic transducers with spherical curved surfaces. Examples are described in: C R Hill et al, "Review article: High intensity focused ultrasound—potential for cancer treatment", *Br J Radiology*, vol. 68, pp. 1296–1303; I H Rivens et al, "Design of focused ultrasound surgery transducers", *IEEE Trans. Ultras. Ferroelec. Freq. Ctrl.*, vol. 43, pp1023–1031; S Madersbacher et al, "Tissue ablation in benign prostatic hyperplasia with high-intensity ultrasound", *Eur. Urol., vol.* 23 (suppl. 1), pp39–43; and A Gelet et al, "High-intensity focused ultrasound experimentation on human benign prostatic hypertrophy", *Eur. Urol.,* vol. 23 (suppl. 1), pp. 44–47, 1993.

However, a significant disadvantage of using a single focused transducer is its fixed focal length. Since the volume of the ultrasound focus is usually smaller than the volume of tissue to be ablated, a means for mechanically translating the transducer must be incorporated. Since it is possible to ablate approximately 2 cm$^3$ of tissue per hour using a single focused transducer, treatment of a modest tissue volume (say 8 cm$^3$) may require multiple sessions totalling 4 hours. Thus, whilst adequate for experimental studies and preliminary clinical testing, mechanical scanning of a single transducer presents a serious practical limitation that may prevent it becoming a routine clinical procedure.

It is possible to reduce such problems by the use of phased arrays in which a plurality of transducer elements are mounted on a substrate surface and collectively provide a focused beam of ultrasound. Such arrays are generally described in: C A Cain et al, "Concentric-ring and sector-vortex phased-array applicators for ultrasound hyperthermia", *IEEE Trans. Microwave Theory Tech.*, vol. MTT-34, pp542–551; E S Ebbini et al, "A spherical-section ultrasound phased-array applicator for deep localized hyperthermia", *IEEE Trans. Biomed. Eng.*, vol. 38, pp634–643; S Umemura et al, "Acoustical evaluation of a prototype sector-vortex phased-array applicator", *IEEE Trans. Ultrason. Ferroelec. Freq. Contr.,* vol. 39, pp32–38; S A Goss et al, "Sparse random ultrasound phased array for focal surgery", *IEEE Trans. Ultras. Ferroelec. Freq. Ctrl.,* vol. 43, pp. 1111–1121, 1996; E B Hutchinson et al, "Design and optimization of an aperiodic ultrasound phased array for intracavitary prostate thermal therapies", *Med. Phys.,* vol. 23, pp767–776; E B Hutchinson et al, "Intracavitary ultrasound phased array for non-invasive prostate surgery," *IEEE Trans. Ultras. Ferroelec. Freq. Ctrl.,* vol. 43, pp 1032–1042; H Wan et al, "Ultrasound surgery: comparison of strategies using phased array systems", *IEEE Trans. Ultras. Ferroelec. Freq. Ctrl.,* vol. 43, pp. 1085–1097; K Hynynen et al, "Feasibility of using ultrasound phased arrays for MRI monitored non-invasive surgery", *IEEE Trans. Ultras. Ferroelec. Freq. Ctrl.,* vol. 43, pp1043–1053; L R Gavrilov et al, "A method of reducing grating lobes associated with an ultrasound linear phased array intended for transrectal thermotherapy", *IEEE Trans. Ultras. Ferroelec. Freq. Ctrl,* vol. 44, pp1010–1017.

Such phased arrays offer electronically controlled dynamic focusing and the ability to vary and control precisely the range and location of the focus during treatment without moving the array. The use of phased arrays offers means of not only rapidly scanning the ultrasound focus but also of synthesizing fields with multiple simultaneous foci. Their use is expected to reduce the time taken to deliver ablative therapy. Several references above propose the use of phased arrays in which elements are placed on a spherical shell, thereby combining electronic and geometric focusing.

A significant disadvantage of known phased arrays is the unwanted presence of grating lobes and other unpredictable secondary intensity maxima which can potentially lead to injuries to a patient undergoing surgery, where excessive energy is deposited into tissue outside the focal region. Another disadvantage, particularly for extracorporeal, two-dimensional arrays, is complexity and potentially relatively high cost.

The need to reduce grating lobes is common to all therapeutic arrays reported to date, and several techniques including apodization, broad banding and the use of subsets of elements have been investigated. The use of a random distribution of different sized elements in a linear phased array has been investigated. Grating lobe levels associated with an array with an aperiodic distribution of elements are approximately 30%–45% less than those associated with periodic centre-to-centre spacing.

It is an object of the present invention to provide an ultrasound transducer array which significantly improves the ability to control precisely the range and location of the focus of the ultrasound energy.

It is a further object of the present invention to provide an ultrasound transducer array which significantly improves the ability to vary the range and location of the focus of the ultrasound energy during use without moving the array.

According to one aspect, the present invention provides an array of ultrasound transducer elements dispersed across a substrate surface, for focusing ultrasound energy over a predetermined focal volume, the elements being dispersed over the substrate surface in a quasi-random distribution, the total radiating area of the elements occupying between approximately 40 and 70% of the total array area.

Preferably the frequency of operation of the ultrasound elements and the average diameter of the elements are related according to the expression:

$$d = A \times c / f$$

where d=average diameter of the elements, c=velocity of sound in the medium to be irradiated with the ultrasound energy, lying in the range 1400 to 1600 ms$^{-1}$, f=frequency of ultrasound energy and A is a value lying in the range approximately 0.5 to 5.

Preferably, the transducer array substrate surface is a curved shell in which the transducer elements are adapted to radiate from the concave surface of the shell and in which the array has an average diameter, D, which is greater than or equal to 0.7R where R is the radius of curvature of the shell and in which the value of R lies in the range 70 to 200 mm.

Preferably the frequency f lies in the range 0.5 to 3 MHz, and more preferably lies in the range 0.5 to 2 MHz, or 1 to 2 MHz.

According to another aspect, the present invention provides a method of providing localised ultrasonic heating to tissue within a body, using a phased array of ultrasound transducer elements which are dispersed across a substrate surface to focus ultrasound energy over a predetermined focal volume, comprising the steps of:

dispersing the elements over the substrate surface in a quasi-random distribution, with the total radiating area of the elements occupying between approximately 40 and 70% of the total array area, selecting a frequency of operation of the ultrasound elements and the average diameter of the elements related according to the expression:

$$d = A \times c/f$$

where d=average diameter of the elements, c=velocity of sound in the tissue medium being irradiated with the ultrasound energy, f=frequency of ultrasound energy and A is a value lying in the range approximately 0.5 to 5.

Embodiments of the present invention will now be described by way of example with reference to the accompanying drawings in which.

In preferred embodiments of the present invention, particularly advantageous configurations of ultrasound phased arrays are described. The arrays are mounted on a substrate surface which may, for example, comprise a segment of a spherical surface as will be described. Such optimized phased arrays are ideally suited for extracorporeal ablation or short duration high-intensity hyperthermia.

Also described is a method for calculating which consists of three main steps, namely: (i) calculation of the complex pressure distribution associated with a single plane circular element; (ii) calculation of the total complex pressure distribution associated with an array of these circular elements mounted on a spherical shell; and (iii) calculation of the complex pressure and the normalized intensity distributions for the complete array and analysis thereof.

The complex pressure distribution associated with a single plane circular element can be found using the rectangular radiator method, such as described in K Ocheltree et al, "Sound field calculations for rectangular sources", *IEEE Trans. Ultrason. Ferroelec. Freq. Ctrl.,* vol. 36, pp. 242–248.

Figure 1A:
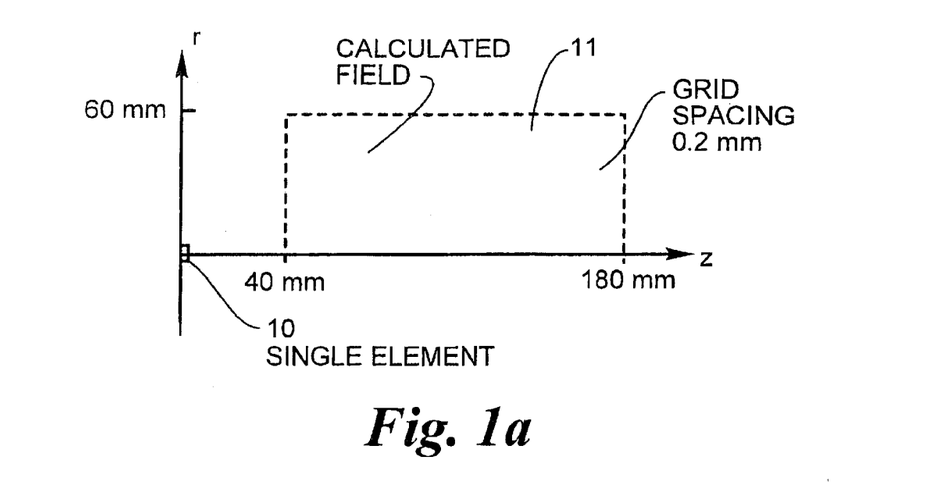
FIGS. 1a and 1b show schematic illustrations of a method used for calculating: a) the field of a single transducer element; and b) the field of an array of transducer elements.
Figure 1B:
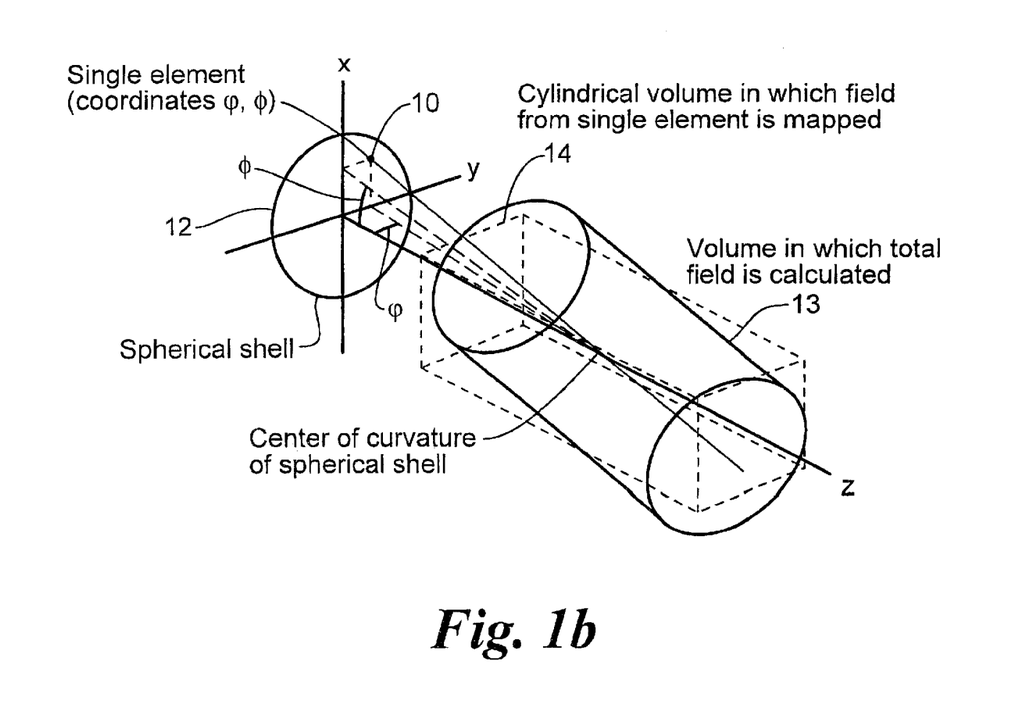

With reference to FIGS. 1a and 1b, square elemental ultrasound radiator elements 10 of side length 0.25 mm are used to describe the radiating surface of each circular element. In all the examples given, ultrasound is assumed to propagate through a uniform medium of density 1000 kg m$^{-1}$ and the speed of sound to be 1500 m s$^{-1}$. More generally, however, the ultrasound is preferably focused in body tissue via a suitable acoustic coupling medium such as water, in which the speed of sound, c, for both media lies in the range 1400 to 1600 m$^{-1}$. The amplitude attenuation coefficient in the tissue is taken to be 11.5 Np m$^{-1}$ MHz$^{-1}$, as described, for example, in F Duck, "Physical Properties of Tissue" London: Academic Press, 1990.

As examples, three frequencies of 1, 1.5 and 2 MHz are used in the calculations and element diameters of 3, 5, 7 and 10 mm are considered. With reference to FIG. 1, by assuming radial symmetry for each circular element 10, its 3-dinensional acoustic field can be found by calculating the complex pressure as a function of axial distance z from the element 10 and distance off the axis, r. Calculations are carried out for z and r over the ranges 4–18 cm and 0–6 cm, respectively, in spatial increments of 0.2 mm, which is found to provide adequate characterization of the spatial distribution.

In the examples, the radius of curvature of a spherical shell on which the elements 10 lie, is 120 mm. The total complex pressure distribution from an array of plane circular elements 10 mounted on the shell 12 is calculated by summing the complex pressure contributions from each element at each point in the 3-dimensional volume of interest 13 as shown in FIG. 1b.

Having found the complex pressure as a function of axial and radial distances for the single element whose centre is defined by the angular co-ordinates φ and (φ (the angles subtended at the centre of curvature in the vertical and horizontal planes by the projection onto the x- and y-axes of the co-ordinates of the element), the values are mapped from the rotated cylindrical volume 14 to points on a 0.2 mm 3-dimension rectangular grid 11 aligned with the Cartesian axes. Calculations are carried out over a volume that extends from z=40 mm to 180 mm axially as shown in FIG. 1a, and from 0 to ±60 mm in the 2 remaining orthogonal directions, ie. for r=60 as shown in FIG. 1a.

Phase distributions at the elements necessary to focus the array at a single point are determined from the paths between the centres of each element and the position of the focus.

The intensity at each grid point is found from the product of the complex pressure and its complex conjugate and the distribution is normalized with respect to the global maximum obtained within the volume of interest.

Calculations of the pressure and intensity field distributions may be carried out using a suitably programmed computer, and the data can be analyzed using, for example, AVS (from Advanced Visual Systems Inc. Waltham, Mass.) running on a Indigo2™ workstation (from Silicon Graphics) and Axum 4.1 (from MathSoft, Inc.) running on a PC.

Three-dimensional intensity distributions can thus be analyzed qualitatively and contour plots in selected planes used for quantitative analyses of the data.

The two-dimensional intensity distributions presented as examples herein represent data in the y-z plane. This plane contains the ultrasound focus when it is not coincident with the centre of curvature and is a "worst case" in terms of the level of grating lobes. Calculations carried out with the focus located in the x-z plane give qualitatively similar results and need not be presented here.

The influence on array performance of several parameters such as the number of elements (64, 128, 256 and 1024), their diameter (3, 5, 7 and 10 mm), ultrasound frequency (1, 1.5 and 2 MHz) and level of sparseness of the elements has been investigated to determine optimum configurations of array. Calculations have been made for arrays 24, 25, 26 with elements 20 quasi-randomly distributed on the shells 21, 22, 23 respectively (FIG. 2) as well as for arrays 34, 35, 36 with elements 20 distributed on the shells 31, 32, 33 in hexagonal and square patterns respectively (FIG. 3). The basic dimensions of the arrays are also presented in the Figures. However, although the locations of the elements are schematically indicated in the drawings, note that the individual element dimensions are not, each element merely being represented by a dot.

In the example of FIG. 2, the configuration of elements 20a on the spherical shell 21 consists of 256 plane circular elements, each 5 mm in diameter. The elements 20 generally occupy a total array area 28, as bounded by the dashed line, of the substrate surface.

The elements are distributed in a quasi-random manner. Preferably, a completely random distribution is modified such that the minimum separation between centres of elements is 5.5 mm, ie. the element edges have a minimum separation of 0.5 mm. Three driving frequencies are considered for this array, being 1, 1.5 and 2 MHz. (Several quasi-random distributions of the elements on the shell have been investigated but the difference in the results for the array of the same configuration is negligible).

A frequency range between 1 and 2 MHz is preferred for ultrasound arrays for therapeutic applications, which represents a compromise between avoiding cavitation effects associated with low frequencies and high attenuation associated with high frequencies. However, frequencies generally in the range 0.5 MHz to 3 MHz also show effective results.

The use of a random distribution of elements 20 is desirable to avoid unwanted artefacts from the periodicity of the array emerging in the energy distribution of the ultrasound. The selection of a quasi-random distribution of elements is preferred for practical reasons to avoid too close a spacing between elements which can cause practical problems with construction. The use of such quasi-random distributions has been found to have minimal effects on the advantages conferred by random arrays particularly where, for example, a minimum spacing between elements of between 0.5 and 1 mm has been used.

Figure 2A:
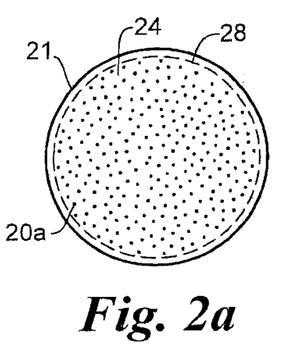
FIGS. 2a, 2b and 2c show schematic drawings of arrays with plane circular elements distributed on a spherical shell in a quasi-random manner.
Figure 2B:
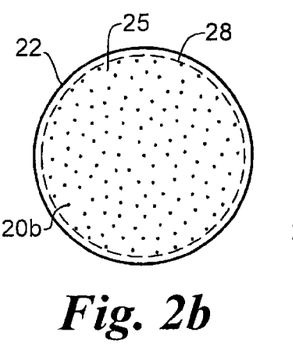
Figure 2C:
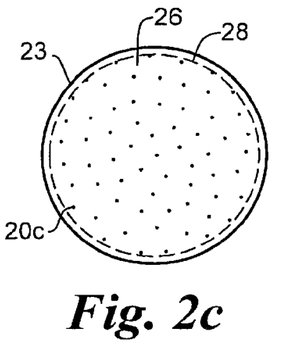

Calculations have also been made for randomly distributed arrays of 128 circular elements 20b, each 7 mm in diameter (FIG. 2b), and of 64 elements 20c, each 10 mm in diameter (FIG. 2c). The frequency in both cases is 1.5 MHz and the minimum separation between centres of elements is 8 and 11 mm, respectively. All of the arrays presented in FIG. 2 have an active area (total area of transducer elements) of approximately 50 cm$^2$ and so, in theory, are able to provide approximately the same acoustic power.

Figure 3A:
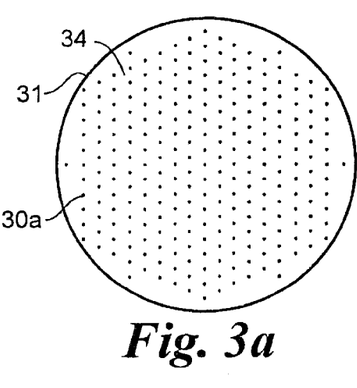
FIGS. 3a, 3b and 3c show schematic drawing of arrays with circular elements distributed on a spherical shell in regular patterns with: a) comprising 255 elements distributed in an hexagonal pattern; b) comprising 256 elements distributed in a square pattern; and c) comprising 1024 elements distributed in a square pattern.
Figure 3B:
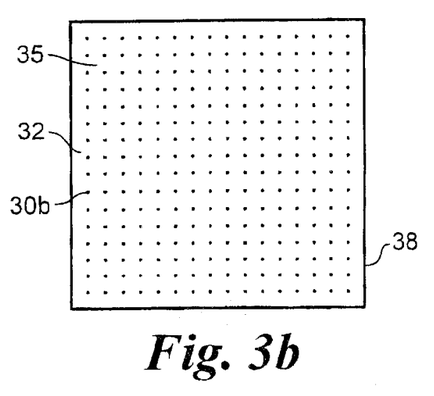
Figure 3C:
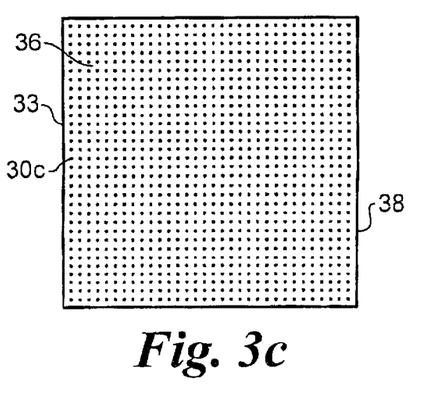
Figure 4A:
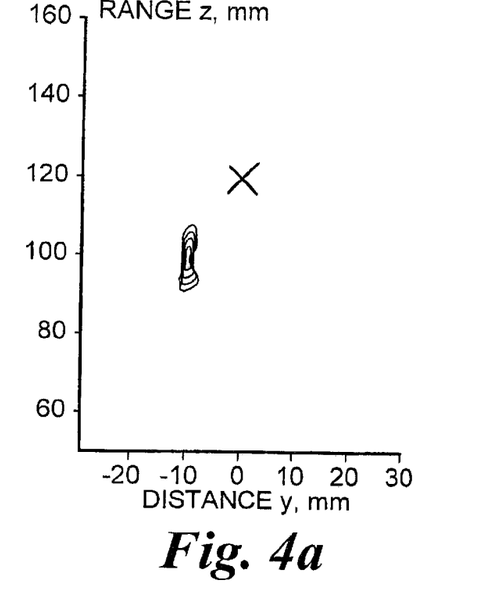
FIG. 4 shows examples of ultrasound intensity field distributions and criteria used for estimating the quality of the intensity distributions for focuses located at: a)=(0,−10, 100 mm); b)=(0, 0, 130 mm); c)=(0, 0, 135 mm); d)=(0, −20, 80 mm)
Figure 4B:
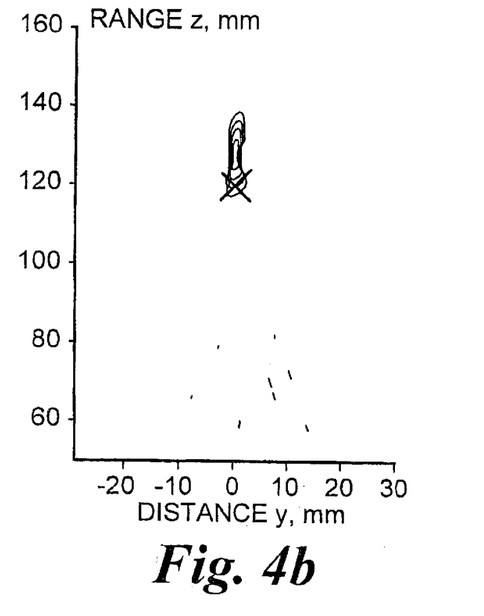
Figure 4C:
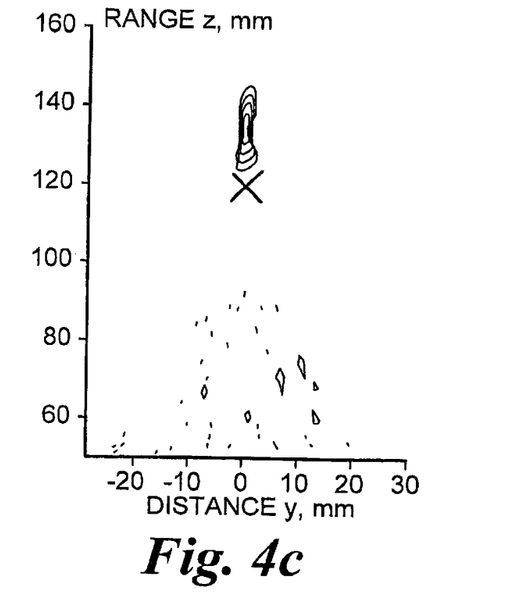
Figure 4D:
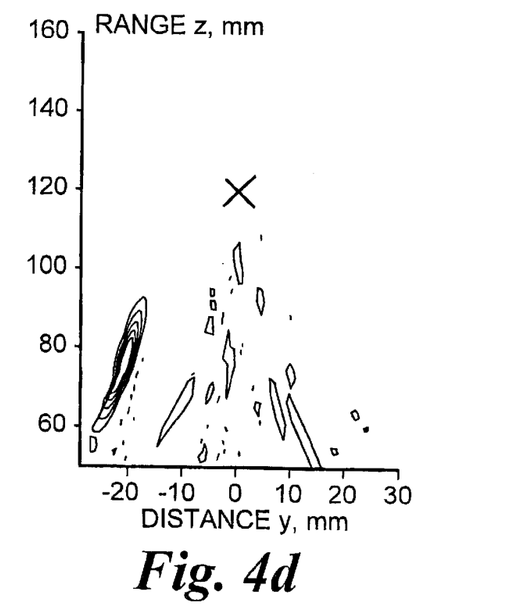

FIG. 3a shows a schematic representation of an array 34 consisting of 255 elements 30a in an hexagonal configuration, each 5 mm in diameter, placed on a spherical shell 31. The minimum separation between element centres is 6.5 mm. FIG. 3b shows an array 35 of 256 of the same sized elements 30b placed on the shell 32 in a square configuration with centre to centre spacing of 6 mm. In both cases, the frequency used is 1.5 MHz and the active area is approximately 50 cm$^2$. FIG. 3c shows an array 36 consisting of 1024 elements 30c, each 3 mm in diameter, distributed on the shell 33 in a square configuration. In this case the centre to centre spacing is 4 mm, the active area is approximately 72 cm$^2$ and the frequency used is 1.5 MHz.

Four exemplary criteria are selected to assess the "quality" of the normalized intensity distributions calculated for the various arrays. First, an intensity distribution is deemed to be "grade A" when intensity $I \geq 0.1\ I_{max}$ occurs only within the focal region and is absent in the remainder of the plane investigated. In other words, the intensity distribution falls to 10% or less of the peak intensity, outside the focal region.

As measures of poorer performance the following criteria are selected. The intensity distribution is described as "grade B" when there are fewer than 10 localized areas in which the intensity is in the range $0.1 \leq I \leq 0.15\ I_{max}$ outside the focal area in the plane considered. Intensity distributions with more than 10 localized areas outside the focal area in the plane considered in which $0.1 \leq I < 0.15\ I_{max}$ are classified "grade C". Finally, further discrimination amongst poor intensity distributions is provided by a "grade D" classification for those where there is at least one localized area in which $I \geq 0.2\ I_{max}$.

For safe delivery of treatment, it is believed that the level of the intensity in grating lobes should be at least 8–10 dB lower than that in the main lobe. Thus an A-graded intensity distribution may be considered good for clinical applications. An intensity distribution having grade D quality is likely unacceptable for clinical use from the point of view of patient safety. The boundary between clinical usefulness and otherwise for distributions characterized as grade B or C is not sharp.

Examples of intensity distributions for the design parameters above are now presented.

FIG. 4 shows examples of intensity distributions for the random array shown in FIG. 2a driven at a frequency 1.5 MHz. FIG. 4a corresponds to an "A" grade quality intensity distribution, FIG. 4b corresponds to a "B" grade quality intensity distribution, FIG. 4c corresponds to a "C" grade quality intensity distribution and FIG. 4d corresponds to a "D" grade quality intensity distribution. In each case, the symbol x marks the location of the centre of curvature of the shell. The focuses are located at: a)=(0,−10, 100 mm); b)=(0, 0, 130 mm); c)=(0, 0, 135 mm); d)=(0,−20, 80 mm).

The graphs illustrate the dependence of quality of an intensity distribution on the location of the steered focus. Nine contours (10–90% $I_{max}$ in increments of 10% $I_{max}$) are drawn inside the focal region. Characterization of the intensity distributions in the remainder of the plane outside the focal region is assessed in terms of contours at 10–20% $I_{max}$ in increments of 5% $I_{max}$ and, in a few cases, by contours at 10–20% $I_{max}$ in increments of 2% $I_{max}$.

Figure 5A:
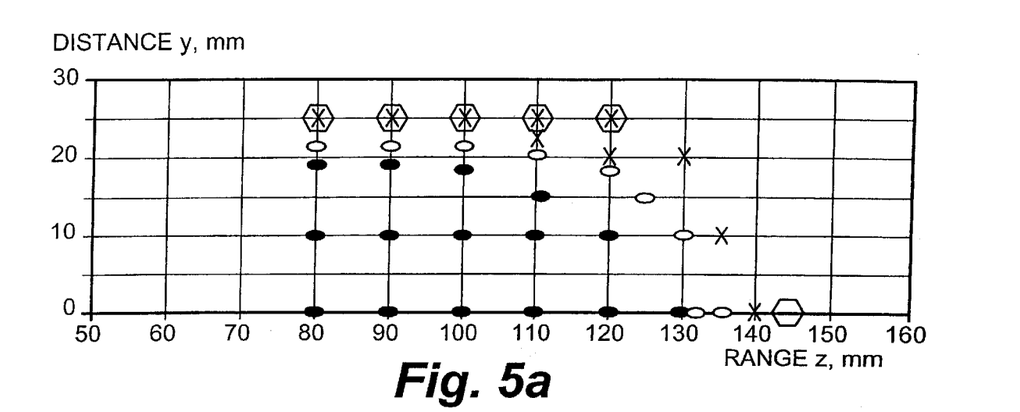
FIG. 5 shows a summary of results of calculations and quality assessment of intensity distributions associated with a random array of 256×5 mm diameter elements at frequencies: a) 1 MHz; b) 1.5 MHz; and c) 2 MHz.
Figure 5B:
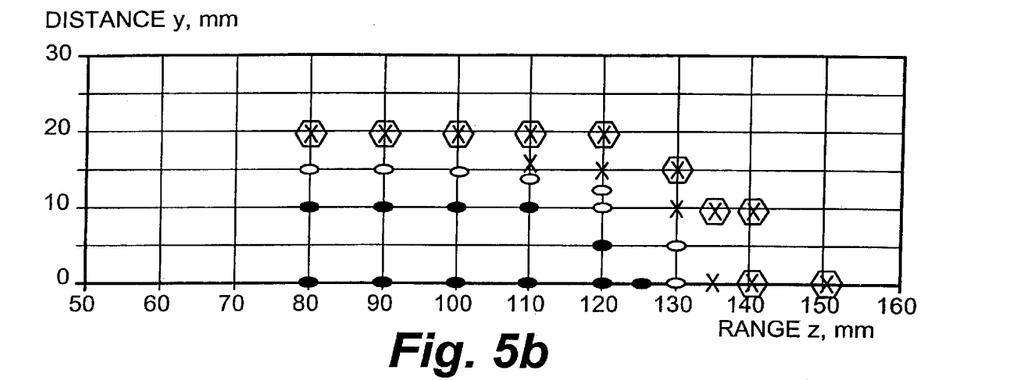
Figure 5C:
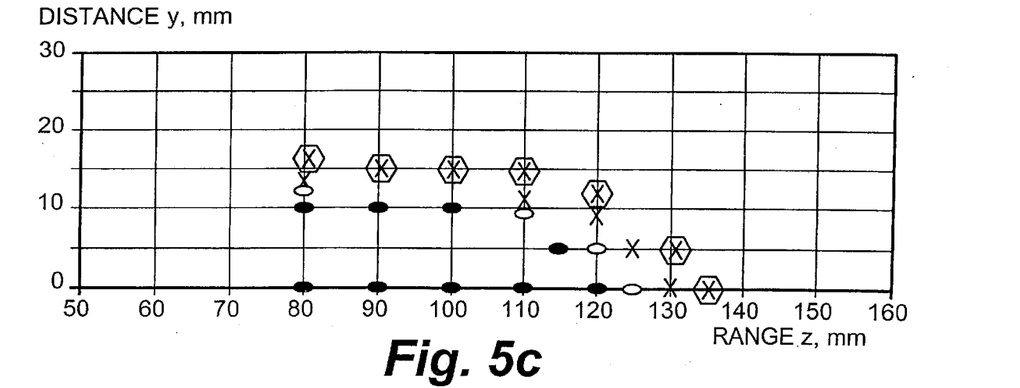

Characterization of the intensity distributions associated with this array driven at 1, 1.5 and 2 MHz is summarized in FIG. 5. FIG. 5a shows the intensity distribution for the 256×5 mm elements driven at 1 MHz; FIG. 5b shows the intensity distribution for the 256×5 mm elements driven at 1.5 MHz; and FIG. 5c shows the intensity distribution for the 256×5 mm elements driven at 2 MHz. The quality rating is given as grade "A" (filled circle ●); grade "B" (open circle ○); grade "C" (cross x) and grade "D" (crossed circle ⊗).

FIG. 5 as well as the following FIGS. 6 and 7 present data for displacements in the positive y-direction. In the cases of random arrays with large enough numbers of elements, calculations carried out for foci displaced in the negative y-direction yield results which are qualitatively similar.

Figure 6A:
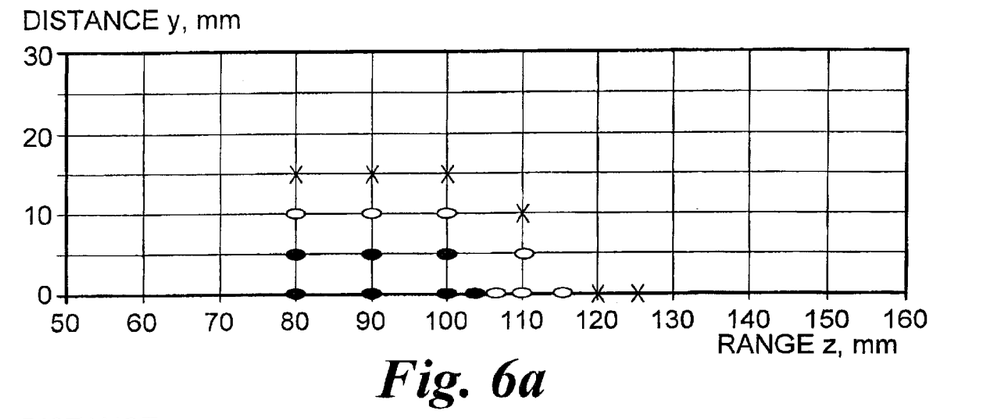
FIG. 6 shows an assessment of the quality of intensity distributions associated with: a) a random array consisting of 128 elements, randomly selected from the array of FIG. 2a; b) an array of 128×7 mm diameter randomly distributed circular elements; and c) an array of 64×10 mm diameter randomly distributed circular elements.

FIG. 6a illustrates the effect of increasing the sparseness in the random array of 5 mm diameter elements in that the characterization of the intensity distribution shown is for the case when half of 256 randomly distributed elements are switched off randomly (ie. a 128 element array). The driving frequency is 1.5 MHz.

Figure 6B:
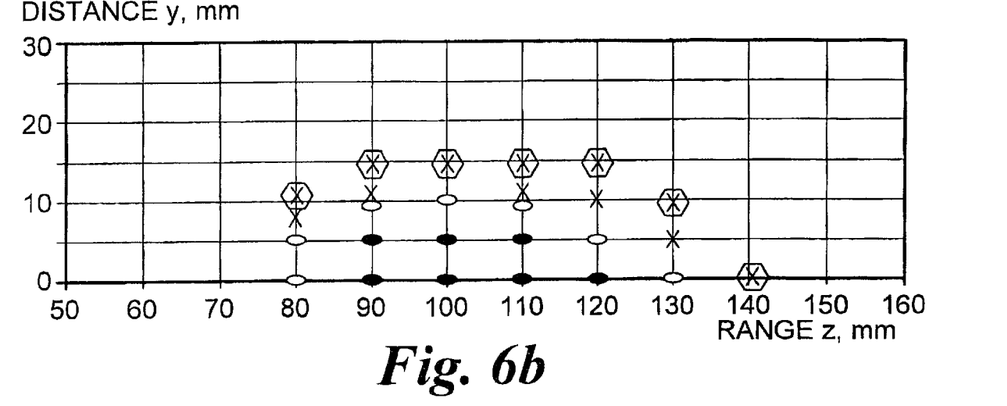
Figure 6C:
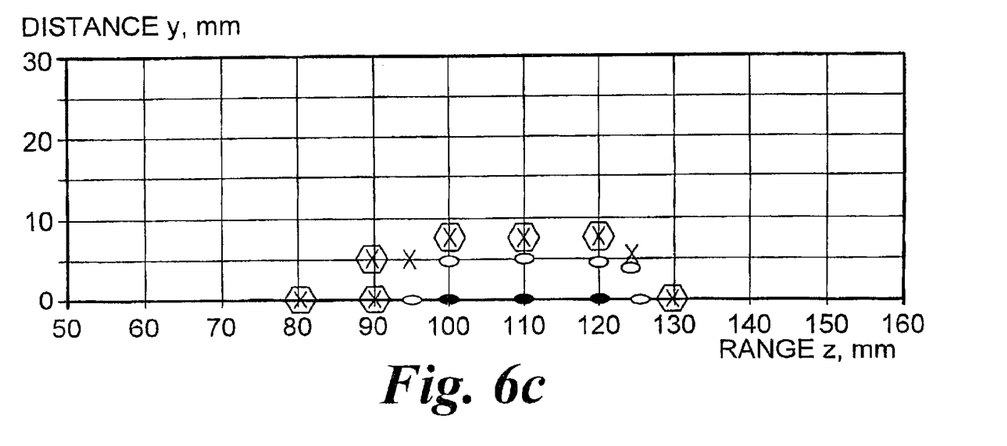

Assessment of the intensity distributions for the random arrays of 128×7 mm diameter circular elements array (shown in FIG. 2b) driven at a frequency of 1.5 MHz are shown in FIG. 6b. FIG. 6c illustrates similar data for the random array of 64×10 mm diameter circular elements shown in FIG. 2c driven at 1.5 MHz. The symbol nomenclature is as described for FIG. 5.

Figure 7A:
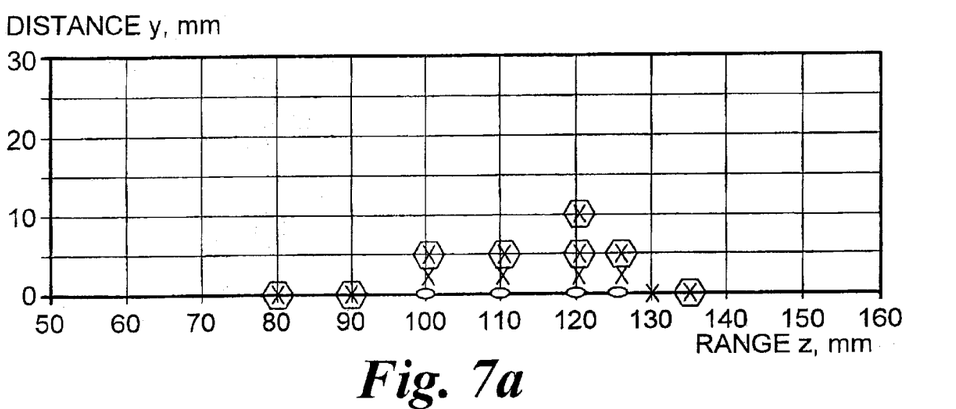
FIG. 7 shows an assessment of the intensity distributions associated with regular arrays of: a) 255 elements, each 5 mm diameter, distributed on the shell in an hexagonal pattern; b) 256 elements, each 5 mm diameter, distributed on the shell in a square pattern; c) 1024 elements, each 3 mm diameter, distributed on the shell in a square pattern.
Figure 7B:
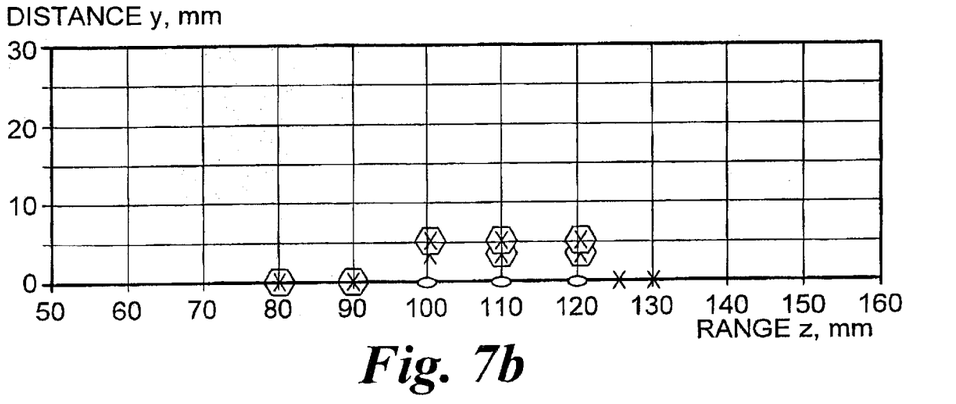
Figure 7C:
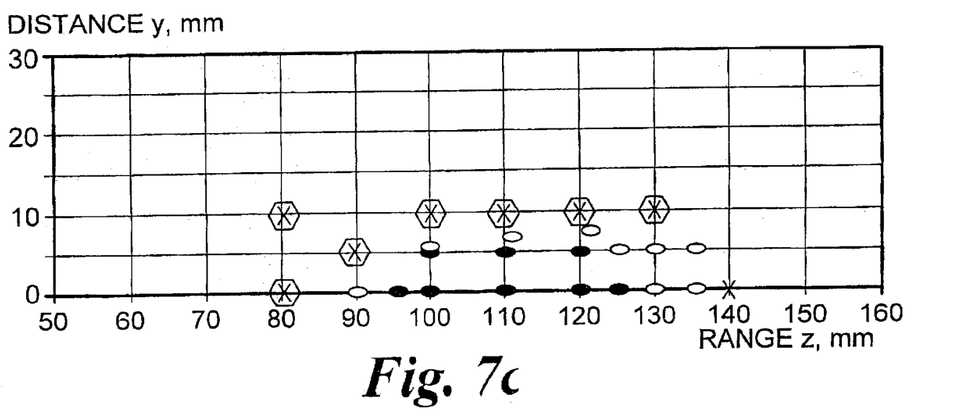

FIG. 7 shows the assessment of intensity distributions for arrays with regular spatial distributions of elements illustrated in FIGS. 3(a)–(c). Thus, FIG. 7a represents a 255×5 mm element array distributed on a shell in a hexagonal pattern; FIG. 7b represents a 256×5 mm element array distributed on a shell in a square pattern; and FIG. 7c represents a 1024×3 mm element array distributed on a shell in a square pattern. The driving frequency is 1.5 MHz in all these cases. The symbol nomenclature is as described for FIG. 5.

Figure 8:
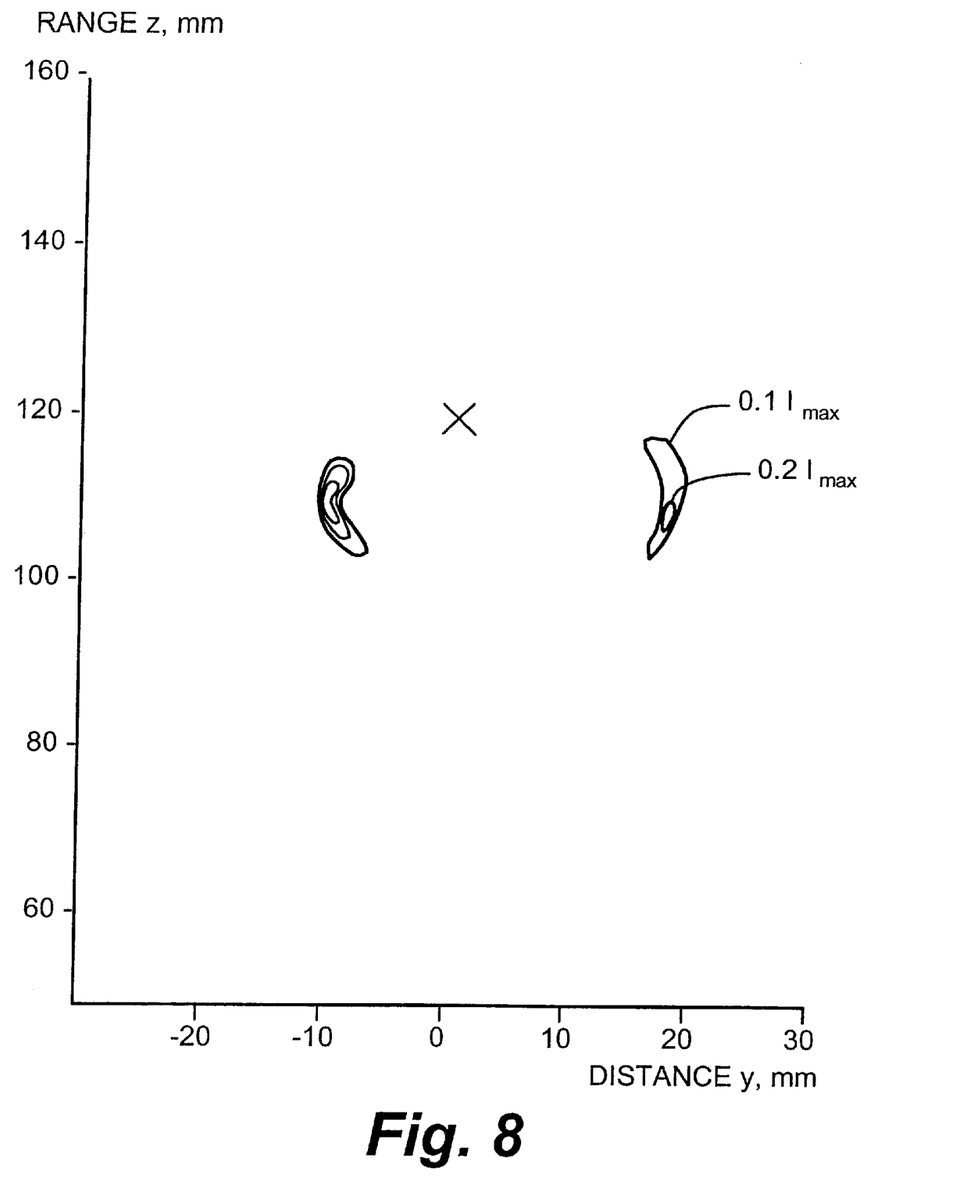
FIG. 8 shows the intensity distribution for a regular square pattern array of 1024×3 mm diameter elements.

FIG. 8 shows the intensity distribution for the 1024 element array (FIG. 3c) focused at a range of 110 mm and 10 mm off axis. The centre to centre distance of the elements is 4 mm and the driving frequency is 1.5 MHz. The focus is located at (0, −10, 110 mm). The cross symbol x corresponds to the centre of curvature of the shell.

The presence of a relatively large high grating lobe, which is typical of the intensity distributions calculated for the regular arrays, is seen. Qualitatively similar results are obtained (but not shown here) for the same array driven at 1 MHz. However in that case, at axial ranges z>120 mm, the grating lobes in the focal plane are located outside the lateral borders of the region over which the intensity distribution is calculated.

Table 1 shows the normalized maximum intensity when the focus is located at the centre of curvature of the spherical shell (0, 0, 120 mm) calculated for each of the arrays considered. Normalization is with respect to the maximum intensity calculated for 1.5 MHz, 256 elements of 5 mm diameter, randomly distributed shell with elements in square patterns.

several centimetres along and off the central axis together with an acoustic power of at least 300–400 W in order to ablate a volume of tissue of practically useful dimensions (eg. 10 cm$^3$) located in deep tissue. It is also desirable to maintain the power transmitted into grating lobes and unwanted secondary maxima ("hot spots") at an acceptably low level (eg. −10 dB below that in the focus).

The practical realization of such an array involves several competing factors. To increase the distance over which the focus may be steered and the volume of tissue treated, it is necessary to decrease the size of the elements to make them less directive. To eliminate grating lobes in a regular array the centre to centre spacing between elements should be less than half the wavelength. On the other hand, to satisfy the required power handling capability, the minimum active area of the array should be approximately 50 cm$^2$ or greater corresponding to an intensity at the elements of approximately 6–8 W/cm$^2$.

The quality of the intensity distributions has been assessed by considering values in the plane containing the focus and within an area of 110 mm (in range) by 60 mm (laterally). The array consisting of 256 plane circular elements, each 5 mm in diameter, distributed in a quasi-random manner and driven at 1 MHz described here can steer the focus up to ±20 mm off centre and at least 50 mm along the central axis, and still achieve a good quality rating (grade A as defined above) and up to ±22 mm off centre and at least 55 mm along the central axis with a grade B rating (see FIG. 5a).

When this array is driven at 1.5 MHz, the distances over which the focus can be steered compatible with A and B ratings is ±10 mm and ±15 mm off centre and 45 and 50 mm along the central axis, respectively (FIG. 5b). It is worth noting that the A-grade criterion used to assess the intensity distributions here is more rigorous than simply using the ratio between the maximum intensity in the grating lobes in the focal plane and that in the focus.

The performance of the array as assessed by the quality of the intensity distribution is dependent upon both the distance of the focus from the centre of curvature and the attenuation. In the examples presented here the attenuation coefficient varied from 1 dB/cm (at 1 MHz) to 2 dB/cm (at 2 MHz). FIG. 5 shows that when the focus is steered beyond the shell's centre of curvature, the quality of the intensity distribution decreases abruptly. It is seen also that the greatest steering of the focus off centre with a grade A quality may be achieved at a range approximately 1–2 cm proximal to the centre of curvature (FIG. 5).

The treatment volume varies from 45 cm$^3$ for a frequency of 1 MHz to 12.5 cm$^3$ for a frequency of 1.5 MHz (FIG. 5a,

TABLE 1

Relative values of the maximum sound pressure $P_{max}$ in the calculated field for several random and regular arrays. The results presented refer to focusing at the centre of curvature (0, 0, 120 mm).

| Random | | | | | | Regular | | |
| --- | --- | --- | --- | --- | --- | --- | --- | --- |
| | | | | | | 255 | 256 | 1024 |
| 256 elements diam 5 mm 1 MHz | 256 elements diam 5 mm 1.5 MHz | 256 elements diam 5 mm 2 MHz | 128 elements diam 5 mm 1.5 MHz | 128 elements diam 7 mm 1.5 MHz | 64 elements diam 10 nm 1.5 MHz | elements diam 5 mm 1.5 MHz hexagonal 0 | elements diam 5 mm 1.5 MHz square | elements diam 3 mm 1.5 MHz square |
| 1.29 | 1 | 0.685 | 0.5 | 1.04 | 1.1 | 0.97 | 0.98 | 1.75 |

An "ideal" ultrasound therapeutic phased array system should preferably provide the ability to steer the focus b). For 2 MHz this "useful" volume decreases to 11 cm$^3$, respectively (FIG. 5c). The maximum sound pressure $P_{max}$ in the field associated with this array decreases with increasing frequency, illustrating the influence of attenuation (Table 1).

In the example, for an array consisting of 256 elements each 5 mm in diameter, the ratio of the total area of elements (active area) to the area of the shell is approximately 51%. A significant deterioration of the array's performance occurs when the sparseness of the array is increased by two times, ie. a 128 element array (FIG. 6a). In this case, not only does the useful treatment volume become much smaller, but there is also a shift towards the array since the greatest range at which the focus could be located compatible with an A-graded intensity distribution rating, is 105 mm. Moreover, the value of $P_{max}$ associated with this array decreases by a factor of approximately two in comparison with $P_{max}$ for the random array consisting of 256 elements (Table 1).

Decreasing the number of randomly distributed elements from 256 to 128 to 64 elements, whilst simultaneously increasing the diameter of the elements (from 5 mm to 7 mm and 10 mm, respectively) to maintain a constant active area also leads to a progressive deterioration of the array's performance (FIGS. 6b and 6c). As can be seen from Table 1, the values of $P_{max}$ are approximately the same for these arrays with a constant active area.

The differences in the qualities of the intensity distributions associated with the array of 128 elements, each 5 mm in diameter, and with the array of 128 elements, each 7 mm in diameter and therefore those of higher directivity at the same frequency, are not great (FIGS. 6a and 6b). However, the two fold difference in the sparseness of these two arrays is reflected in the values of $P_{max}$ achieved (Table 1).

The performance of both arrays consisting of 255 and 256 elements of 5 mm driven at 1.5 MHz in which the elements are distributed as hexagonal or square patterns (FIGS. 7a and 7b) is considerably inferior to that of the 1.5 MHz 256×5 mm elements random array (FIG. 5b). In the cases of the regular arrays, it is possible only to steer the focus 30–35 mm along the central axis and be compatible with a B-graded intensity distribution and even a small shift of approximately 3–5 mm) off the central axis lead to significant deterioration in quality. As assessed here, there is little difference in performance between the hexagonal and square packed arrays (FIGS. 7a and 7b).

The performance of the arrays reported show a substantial improvement compared with sparse random arrays as discussed in the prior art. For example, prior art examples have shown theoretical arrays focused at the geometrical centre of a shell, yielding intensity in the grating lobes in the focal plane of 0.13 $I_{max}$. When the array is focused 5 mm off its central axis this level is increased to 0.6 $I_{max}$. In experimental measurements these levels can be as high as 0.38 $I_{max}$ and 0.9 $I_{max}$, respectively. For randomly located elements on the shell, the prior art has shown theoretical expected levels of intensity in grating lobes in the focal plane of 0.04 $I_{max}$ with no steering and 0.16 $I_{max}$ for steering of ±5 mm.

The array consisting of 1024 elements each 3 mm in diameter and distributed in a square pattern (FIG. 3c) is comparable in terms of number and dimensions of elements to the array discussed in Wan et al. The performance of this regular array driven at 1.5 MHz (FIG. 7c) is poorer than that of the 256×5 mm element random array of FIG. 5b, but comparable with the 128×7 mm element random array of FIG. 6b indicating a possible 8-fold decrease in the number of elements.

There is a marked difference in the character of the intensity distributions associated with arrays with randomly and regularly distributed elements in that grating lobes are absent from the distributions of the former and only secondary intensity maxima outside of the focal area are observed (FIG. 4). In the cases of the regular arrays, relatively high intensities corresponding to grating lobes in the focal plane are seen, whilst secondary intensity maxima are absent typically for small shifts of the focus off the central axis (FIG. 8).

Thus, random distribution of elements on a spherical shell leads to marked improvement of the performance of the array compared with cases in which regular hexagonal or square packing is used. As an example, a random array consisting of 256 circular elements of 5 mm in diameter, driven at 1–2 MHz and placed on a spherical shell of the radius of curvature 120 mm such that the maximum distance between centres of elements is 100 mm, provides good performance for applications of thermal therapies.

Such a random array also achieves comparable performance with a regular array whilst providing a several-fold reduction in the number of elements used (up to 8 fold in the examples given). Similarly, the application of the random arrays with the definite combination of their parameters results in the significant improvement of the quality of the performance with the same number of elements in comparison with regular arrays.

In a general aspect, significant improvements in the performance of ultrasound transducer arrays 10 are obtained by providing a random or quasi-random distribution of array elements 20, and by using an element sparseness or dispersion in which the total radiating area of ultrasound element comprises between 40 and 70% of a total array area 28 of a substrate surface which is occupied by the elements.

Preferably the substrate comprises a curved shell 21 in which the elements 20 radiate ultrasound from the concave surface of the shell. Preferably also, the radius of curvature of the shell surface is in the range 70 to 200 mm. The diameter of the total array area 28 is preferably equal to or greater than 0.7×R where R is the radius of curvature of the shell. The number of elements is defined from the area of the transducer, the sparseness and the area of the element.

A flat substrate can be used rather than a curved shell, although the focus volume will generally then be larger and the steerability will generally be lower in this case.

The number of elements 20 used in the array is determined according to the total array area 28, the sparseness of the elements 20, and the individual element sizes chosen.

Preferably, the array is further optimized by ensuring that the ultrasound frequency f and the diameter d=A×c/f where A lies in the range 0.5 to 5, and c is the speed of sound in the medium to be irradiated. The expression "diameter" d, where non-circular elements are used, is taken to mean the approximate average diameter of the element and, where different element types or sizes are used in an array, means the average diameter of element, averaged over all elements.

In preferred embodiments, the number of transducer elements 20 lies in the range 64 and 1024 and the average element diameter lies in the range 3 to 10 mm.

Focal regions of grade "A" standard can thus be achieved, and ranges of distances over which the focus is electronically steerable of 50–60 mm in a longitudinal direction and up to ±20 mm (at 1 MHz, or up to ±10 mm at 2 MHz) in a lateral direction, orthogonal to the central axis of the shell.

Each element 20 in the ultrasound transducer array 24–26 as described above is coupled to an electronic driver circuit according to known principles, which driver circuit can control the amplitude, power and phase of the ultrasound energy. The shape and positioning of the focal region is determined by the overall combination of phase and amplitude of each of the elements. In the preferred embodiments described, an eight-bit resolution of phase for each element is used, ie. each element can be addressed in phase to an accuracy of 1 part in $2^8$ over the 360° range, although for the best configurations of array, as low as a four-bit phase resolution can be used and still obtain grade "A" distribution with steerability.

What is claimed is:

1. An array of ultrasound transducer elements dispersed across a substrate surface having a total array area, for focusing ultrasound energy over a predetermined focal volume, the elements being dispersed over the substrate surface in a quasi-random distribution, and having a total radiating area of the elements occupying between approximately 40 and 70% of the total array area.

2. An ultrasound transducer array according to claim 1 further including means for driving said transducer elements at a predetermined frequency of operation, in which an average diameter of the elements and the frequency of operation are related according to the expression:

$$d = A \times c/f$$

where d=average diameter of the elements, c=velocity of sound in the medium to be irradiated with the ultrasound energy, lying in the range 1400 to 1600 ms$^{-1}$, f=frequency of ultrasound energy and A is a value lying in the range approximately 0.5 to 5.

3. An ultrasound transducer array according to claim 1 having a frequency f lying in the range of 0.5 to 3 MHz.

4. An ultrasound transducer array according to claim 3 having a frequency f lying in the range of 0.5 to 2 MHz.

5. An ultrasound transducer array according to claim 4 having a frequency f lying in the range of 1 to 2 MHz.

6. An ultrasound transducer array according to claim 1 in which the substrate surface comprises a curved shell having a radius of curvature R.

7. An ultrasound transducer array according to claim 6 in which the transducer elements are adapted to radiate from a concave surface of the shell.

8. An ultrasound transducer array according to claim 7 in which the array has an average diameter, D, which is greater than or equal to 0.7R where R is the radius of curvature of the shell.

9. An ultrasound transducer array according to claim 6 in which the value of R lies in the range 70 to 200 mm.

10. An ultrasound transducer array according to claim 7 in which the value of R is approximately 120 mm.

11. An ultrasound transducer array according to claim 1 having a minimum spacing between transducer elements in the array of 0.5 mm.

12. An ultrasound transducer array according to claim 1 in which the transducer elements each have an average diameter between 3 and 10 mm.

13. An ultrasound transducer array according to claim 1 in which the number of elements lies in the range 64 to 1024.

14. An ultrasound transducer array according to claim 1 in which the array is a phased array.

15. An ultrasound transducer array according to claim 1, further including drive means for controlling the phase and amplitude of ultrasound output of each of the elements of the array.

16. An ultrasound transducer array according to claim 15 in which said drive means is adapted to resolve phase differences between elements of the array with a resolution of $2^8$.

17. An ultrasound transducer array according to claim 15 in which said drive means is adapted to resolve phase differences between elements of the array with a resolution of between $2^4$ and $2^7$.

18. A method of providing localised ultrasonic heating to tissue within a body using a phased array of ultrasound transducer elements which are dispersed across a substrate surface, having a total array area, to focus ultrasound energy over a predetermined focal volume, comprising the steps of:

dispersing the elements over the substrate surface in a quasi-random distribution, with a total radiating area of the elements occupying between approximately 40 and 70% of the total array area, selecting a frequency of operation of the ultrasound elements and an average diameter of the elements related according to the expression:

$$d = A \times c/f$$

where d=average diameter of the elements, c=velocity of sound in the tissue medium being irradiated with the ultrasound energy, f=frequency of ultrasound energy and A is a value lying in the range approximately 0.5 to 5.

19. The method according to claim 18 in which the frequency f lies in the range 0.5 to 3 MHz.

20. The method according to claim 19 in which the frequency f lies in the range 0.5 to 2 MHz.

21. The method according to claim 20 in which the frequency f lies in the range 1 to 2 MHz.

* * * * *